United States Patent [19]

Bacus et al.

[11] Patent Number: 5,252,487
[45] Date of Patent: Oct. 12, 1993

[54] METHOD AND APPARATUS FOR DETERMINING THE AMOUNT OF ONCOGENE PROTEIN PRODUCT IN A CELL SAMPLE

[75] Inventors: James W. Bacus; Sarah S. Bacus, both of Hinsdale, Ill.

[73] Assignee: Cell Analysis Systems, Inc., Lombard, Ill.

[21] Appl. No.: 9,378

[22] Filed: Jan. 27, 1993

Related U.S. Application Data

[63] Continuation of Ser. No. 354,660, May 19, 1989, abandoned.

[51] Int. Cl.$^5$ .................... G01N 21/59; G01N 33/50
[52] U.S. Cl. ........................................ 436/63; 436/86; 436/164; 436/174; 436/813; 422/68.1; 422/82.09; 356/39; 382/6
[58] Field of Search ............... 436/8, 15, 63, 86, 172, 436/174, 811, 813, 164, 536; 356/39, 40; 424/3; 382/6; 422/82.05, 82.09, 93, 68.1

[56] References Cited

U.S. PATENT DOCUMENTS

| | | | |
|---|---|---|---|
| 4,097,845 | 6/1978 | Bacus | 356/39 X |
| 4,725,538 | 2/1988 | Senger | 436/813 X |
| 4,741,043 | 4/1988 | Bacus | 356/39 X |
| 4,751,188 | 6/1988 | Valet | 356/39 X |
| 4,782,015 | 11/1988 | Allison et al. | 436/813 X |
| 4,812,909 | 3/1989 | Yokobayashi et al. | 382/6 X |
| 4,847,910 | 7/1989 | Sakuraba et al. | 382/6 |
| 4,887,892 | 12/1989 | Bacus | 356/39 X |
| 4,998,284 | 3/1991 | Bacus et al. | 382/6 |

*Primary Examiner*—James C. Housel
*Assistant Examiner*—Jeffrey R. Snay
*Attorney, Agent, or Firm*—Fitch, Even, Tabin & Flannery

[57] ABSTRACT

An apparatus and method for determining an amount of oncogene protein product copies in a cell includes an optical conversion module for measuring an amount of optically enhanced DNA in a cell sample. A subsystem for measuring an amount of an optically enhanced oncogene protein product protein product is coupled to the DNA measuring means. A subsystem for comparing the measured DNA amount and measured oncogene protein product protein product amount produces a oncogene protein product copy measurement which is fed to an output device for producing an output indicative of the amounts of the oncogene protein product in the cells of the cell sample.

6 Claims, 9 Drawing Sheets

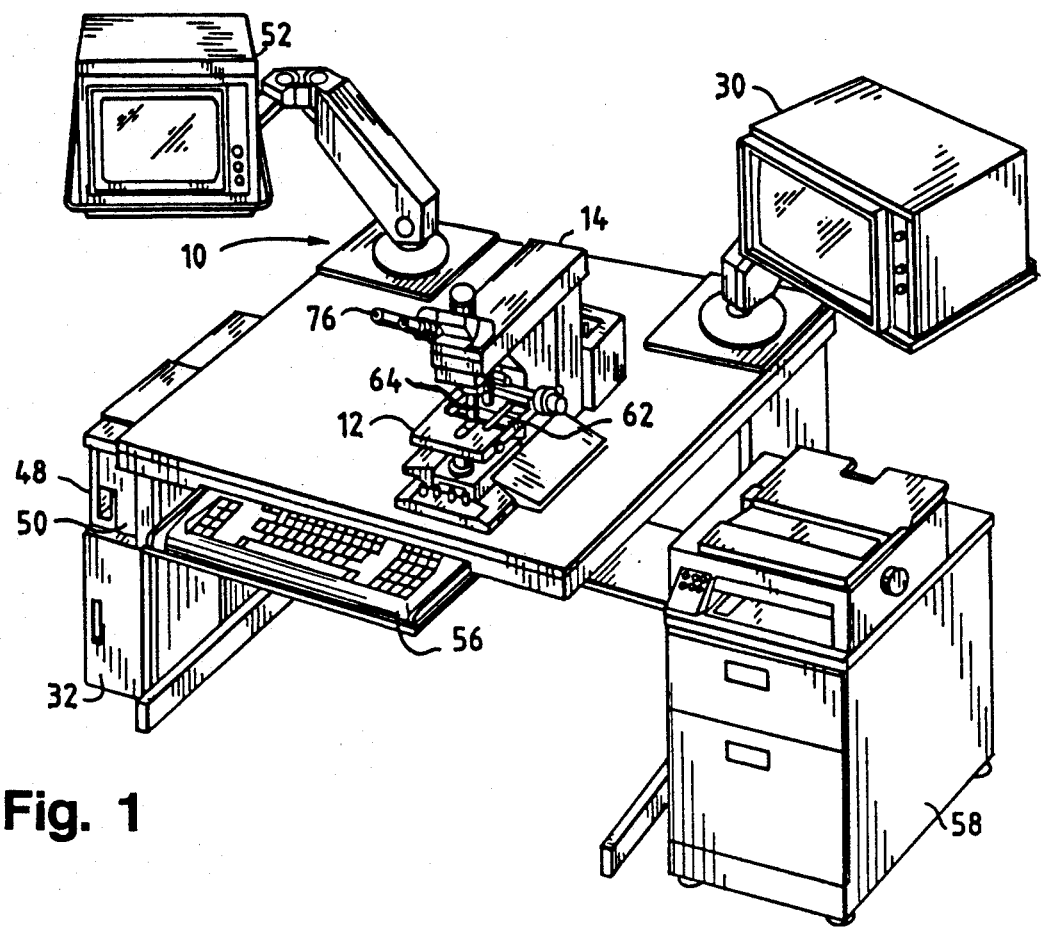
Fig. 1
Fig. 3
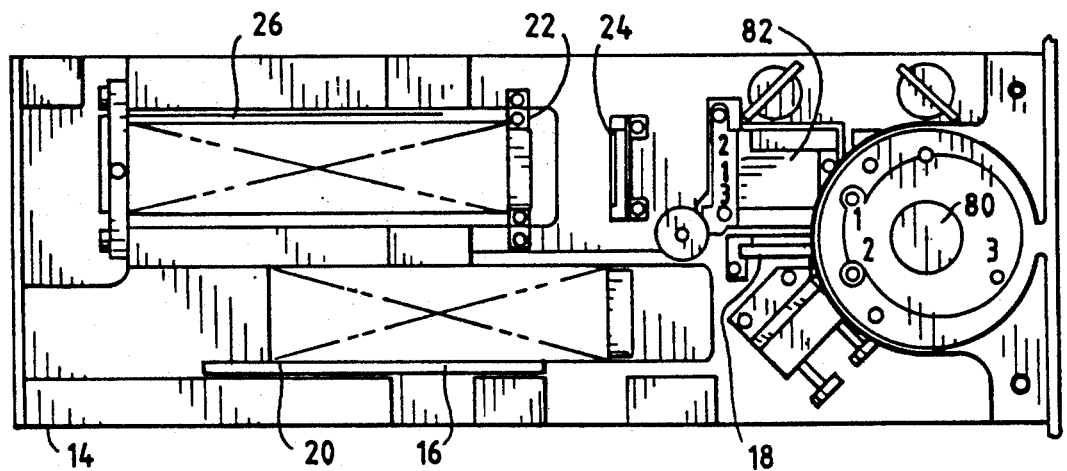

WHITE LIGHT IMAGE

620 NANOMETER IMAGE

500 NANOMETER IMAGE

Fig. 10

QUANTITATIVE CYTOPLASMIC ANTIGEN
CALIBRATION SCREEN

SUN MAY 14 17:44:11 1989

PATIENT ID: 8-15-89 CONTROL CELLS
ACCESSION #:
NUCLEAR STAIN BASED ON 20 PICOGRAMS DNA
CYTOPLASMIC PROTEIN STAIN BASED ON 3.5 PG PROTEIN
NUCLEI: PEAK VALUE  23542   CYTOPLASM: PEAK VALUE  62475
    CV        0.12%          CV       0.23%

CELL COUNT  14

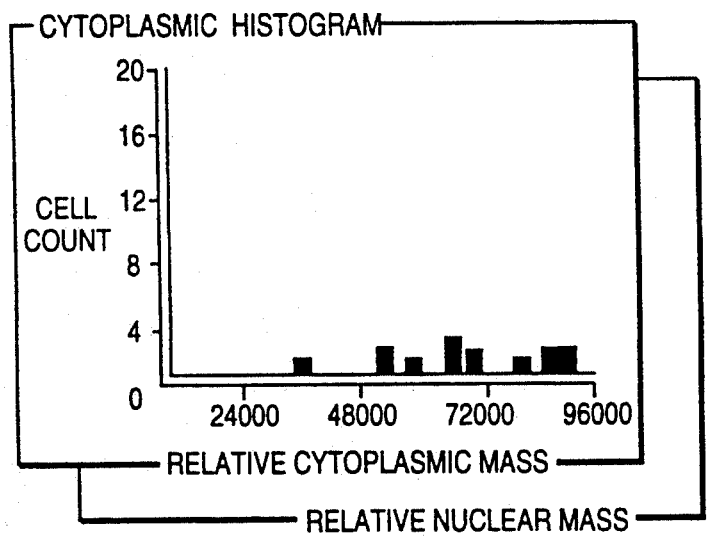

NUC BOUNDARY
CYT BOUNDARY
SWITCH
LABEL
SET LIGHT
CHECK LIGHT
SET XY
BKGRND LIGHT

MEASURE
PLOT
XY LIVE
ANALYZE
CLEAR
HELP
EXIT

Fig. 11

QUANTITATIVE CYTOPLASMIC ANTIGEN  
CALIBRATION SCREEN

SUN MAY 14 17:46:09 1989

PATIENT ID: 8-15-89 CONTROL CELLS  
ACCESSION #:  
NUCLEAR STAIN BASED ON 20 PICOGRAMS DNA  
CYTOPLASMIC PROTEIN STAIN BASED ON 3.5 PG PROTEIN  
NUCLEI: PEAK VALUE  23542   CYTOPLASM: PEAK VALUE  62475  
    CV        0.12%          CV       0.23%

CELL COUNT  14

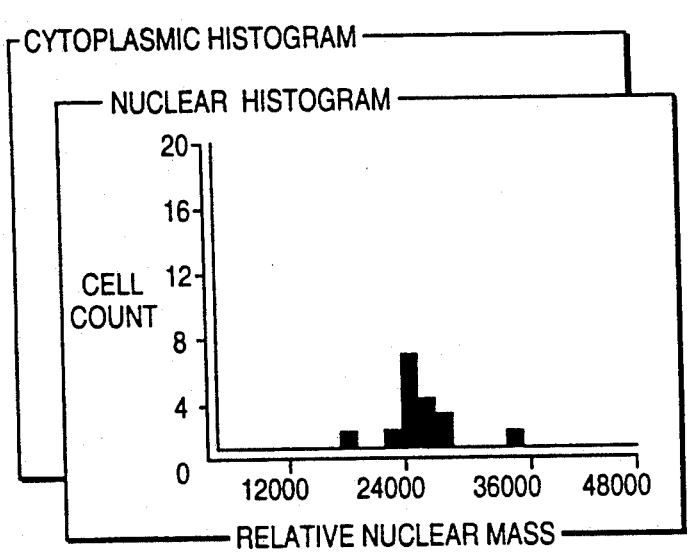

NUC BOUNDARY  
CYT BOUNDARY  
SWITCH  
LABEL  
SET LIGHT  
CHECK LIGHT  
SET XY  
BKGRND LIGHT

MEASURE  
PLOT  
XY LIVE  
ANALYZE  
CLEAR  
HELP  
EXIT

Fig. 13

QUANTITATIVE ONCOGENE PRODUCT
ANALYSIS SCREEN

TUE MAY 16  19:26:55 1909

PATIENT ID:  3-15 89
ACCESSION #:
AVERAGE PICOGRAMS DNA PER CELL  13.52

```
┌─ TOTAL ─────────────────────────────┐
│ TOTAL FIELD COUNT    5              │
│ 0.1062  PG PROTEIN PRODUCT / PG DNA │
│ STANDARD DEVIATION 0.203            │
│ 1.4357  PG PROTEIN PRODUCT/ CELL    │
│ STANDARD DEVIATION 0.2773           │
└─────────────────────────────────────┘
```

```
┌─────────────────────────┐
│ LABEL                   │
│ CHECK LIGHT             │
│ NUCLEAR THRESHOLD       │
│ CYTOPLASMIC THRESHOLD   │
│ MEASURE                 │
│ MERGE                   │
│ XY LIVE                 │
│ DISPLAY XY              │
│ CLEAR DATA              │
│ DISAPEAR                │
│ HELP                    │
│ EXIT                    │
└─────────────────────────┘
```

```
┌─ SINGLE ────────────────────────────┐
│ 0.0968  PG PROTEIN PRODUCT/ PG DNA  │
│ 1.3091  PG PROTEIN PRODUCT/ CELL    │
└─────────────────────────────────────┘
```

METHOD AND APPARATUS FOR DETERMINING THE AMOUNT OF ONCOGENE PROTEIN PRODUCT IN A CELL SAMPLE

This application is a continuation of application Ser. No. 07/354,660 filed May 19, 1989, now abandoned.

BACKGROUND OF THE INVENTION

The invention relates to a system for performing an assay of a cell sample to provide an accurate quantitative analysis of a characteristic of the cells which have been sampled. More particularly, the invention is directed to a system which receives images of stained cells and enhances the cell images prior to further processing to determine an amount of oncogene protein product in the cells of a cell sample.

One of the problems which faces pathologists in their clinical practice is that of determining whether a cell sample taken from a patient during a biopsy procedure or the like is benign, malignant and if malignant the classification or cell type. Although a surgeon may have a good intuition about the type of tissue mass which he has removed, nevertheless he must confirm his preliminary diagnosis with a histological examination of the cell sample removed from the patient. The histological examination entails cell staining procedures which allow the morphological features of the cells to be seen relatively easily in a light microscope. A pathologist after having examined the stained cell sample, makes a qualitative determination of the state of the tissue or the patient from whom the sample was removed and reaches a conclusion as to whether the patient is normal, or has a premalignant condition which might place him at risk of a malignancy in the future or has cancer. While this diagnostic method has provided some degree of predictability in the past, it is somewhat lacking in scientific rigor since it is heavily reliant on the subjective judgement of the pathologist. In addition, it is sometimes difficult for the practitioner to determine the stage which the tumor has reached. Such a determination often allows the clinician to select a particular treatment by balancing the tumor's resistance to therapy with the potential harm resulting from the selected therapy.

Attempts have been made to automate the cellular examination process. In U.S. Pat. No. 4,741,043 to Bacus for Method and Apparatus for Image Analyses of Biological Specimens, an automated method and a system for measuring the DNA of cells are disclosed which employ differential staining of the DNA in cell nuclei with a Feulgen Azure A stain and image processing.

U.S. application Ser. No. 315,289, filed Feb. 24, 1989, now U.S. Pat. No. 5,086,476 for Method and Apparatus for Determining a Proliferation Index of a Cell Sample to Bacus, assigned to the instant assignee, discloses a system for determining the proliferation index of cells by microscopic examination of cell samples which have been stained with a proliferation substance stain and a nuclear stain. The system includes a computer coupled to a pair of monochrome television cameras, which receive optically filtered images of the magnified cell images, and an image processor. The system computes the proliferation index from the optical characteristics of the stained cell sample.

Recently certain genes have been discovered that appear to contribute to the onset and growth of cancers. These genes, known as oncogenes and proto-oncogenes, also may contribute to the growth and development of human beings in the early stages of their lives. Ongoing research has found that certain of these oncogenes seem to be related to specific cancers. One of them, the neu HER-2 proto-oncogene, appears to be related to human breast and ovarian cancers. It has also recently been found that neu HER-2 proto-oncogenes and the oncogene protein product that is expressed from neu HER-2 appear, when in elevated amounts, to be correlated with the virulence of the cancer, Slamon D.J. et al., "Studies of the HER-2/neu Proto-oncogene in Human Breast and Ovarian Cancer," *Science* Vol. 244, pp. 707-712, May 12, 1989. Thus the ability to quantitate the amount of neu HER-2 proto-oncogene and/or its oncogene protein product will allow a clinician to better predict the likelihood of a patient surviving her cancer after completing a selected treatment regimen. By having such information, the clinician will also be better able to select an appropriate treatment regimen to maximize the patient's likelihood of survival.

There would appear to be two ways in which the measurement could be made. The number or amount of neu HER-2 proto-oncogene could be determined in a cell sample using gene probes, which would be expensive and inefficient. Alternatively, the amount of oncogene protein product in the cytoplasm could be measured. While the second choice appears to be more attractive, there are a number of problems encountered with such an approach which prevent easy measurement. The typical tissue specimen biopsied from human breast or ovarian tissue is frozen and then sectioned for microscopic examination. Pathologists favor being able to inspect visually the frozen sections since the portions having malignant cells may be scattered throughout the tissue specimen. It is also difficult to easily determine the locations of cell boundaries in a crowded field because the cancer cells have irregular boundaries. In addition, the monoclonal antibody based stains for visualizing the oncogene protein product work best on frozen sections, as opposed to other types of prepared cell samples. Unfortunately, the sectioned tissue suffers from the problem that while a number of whole cells are present in the section, a number of fractional portions of cells are also present, preventing assaying simply by counting of the cells in an image field of a microscope. It is important to know the sum total of cells being examined because the assay of oncogene protein product is on the basis of the amount of oncogene protein product per cell.

What is needed is a method and apparatus for automatically and quickly assaying the amount of oncogene protein product in the cells of frozen sectioned tissues taken from a human patient.

SUMMARY OF THE INVENTION

The present invention provides a rapid and convenient method and an apparatus for practicing the method for determining the amount of oncogene protein product in the cells of a cell sample. The invention is practiced upon samples of tissue taken from sites of suspected malignancies, in particular human breast and ovarian cancers. The tissue sections are cell samples comprising frozen sections of connected cells. Cell samples may also be made from touch preparations, which are made by touching a freshly microtomed or sectioned surface of a piece of frozen tissue to a microscope slide to which the cells cling.

In particular, the apparatus and method employ a mouse alkaline phosphatase based staining system with an anti-rabbit mouse bridging antibody, wherein rabbit antibodies for a protein product of the genes being assayed are connected to the bridging antibody. In particular, the gene may be neu HER-2, the number of copies of which have been found to be an indicator of the long-term survival of a patient suffering from human breast cancer. The alkaline phosphatase antibodies are complexed with an enzyme, in this embodiment alkaline phosphatase. The cells are contacted with the rabbit primary antibody, which binds only to portions of the cytoplasm of the cells having epitopes identifying them as having the protein product of the neu HER-2 oncogene. After applying the bridging antibody, and the alkaline phosphatase antibody, a stain, in this embodiment Napthol ASTR phosphate and Fast Red KL chromogen, v is placed in contact with the cells having the antibody-alkaline phosphatase conjugate bound to their neu HER-2 protein product sites. The alkaline phosphatase catalyzes a chromogen forming reaction only at the areas where it is bound. The catalyzed chromogen forming reaction produces a red chromogen comprised of a red azo dye at the oncogene protein product sites.

The cells also are stained with a conventional stain for DNA, in this instance a thionine stain using the Feulgen technique which yields a blue stain at cellular sites where there is DNA. The image of the cells is magnified in a light microscope and split into a pair of separated images. The separated images are enhanced by a pair of narrow bandpass optical filters. One of the narrow bandpass optical filters preferentially transmits light having a wavelength at the transmission region of the blue DNA stain thereby producing an optically enhanced oncogene protein product image which only has background and the red chromogen. The background of the oncogene protein product image is composed of the cell nuclei, cytoplasm and the like which have substantially zero optical density. The oncogene protein product sites have a relatively high optical density. Thus the only features which are easily perceivable are the oncogene protein product sites.

The other narrow bandpass optical filter preferentially transmits in the regions of spectral absorption for the blue stain. This filter produces an optically enhanced DNA image of all portions of the cells, with and without neu HER-2 protein product. The apparatus senses the enhanced oncogene protein product image with a first monochrome television camera. The enhanced DNA image is sensed by a second monochrome television camera. Analog signals representative of the images are fed to respective image processors. The image processors convert the analog signals to digitized arrays of pixels which are stored in internal frame buffers. When a tissue section is being examined the apparatus computes a summed optical density of the oncogene protein product image which has high optical density, yielding an area measure weighted by the average pixel optical density for the oncogene protein product in that image field.

In order to avoid the sectioning errors associated with the sectioning techniques used for frozen sections, the invention includes the steps of quantitating a standardized cell sample for DNA in order to determine the linear relationship between the summed optical density of pixels of each cell image in the cell image field having a value indicative of an optical density greater than a selected threshold value. This controls for error which might be introduced by staining variations. A touch preparation is made of cells from the frozen section of the tissue to be examined. This is done by touching the frozen tissue to the warmed slide also having the standardized cells for DNA calibration thereon. The touch preparation comprises a whole cell preparation. In order to obtain the amount of DNA per cell, it is necessary to segregate the pixels associated with each separated cell into separate categories. This is done by the system in conjunction with the human operator. The summed optical density of each of the cell image pixels for each of the sampled cells is also determined in order to determine the average amount of DNA in picograms per cell in the cell sample taken from the patient. This is done in order to remove error introduced by sectioning the tissue sample when the frozen section is made. Thus an average is obtained for the amount of DNA per cell in the cells of the tissue sample. With this information, the clinician then can proceed to the next step in the quantitation of the cytoplasm material, specifically the oncogene protein product. Thus while the whole cell preparation allows an accurate assay of the amount of nuclear material, it cannot be used to assay the cytoplasm. This is because the cytoplasm is relatively fragile and is not completely transferred to the warmed slide in the touch preparation procedure.

Next, a second slide is prepared with a standard cell line thereon having a known amount of DNA per cell and having a known amount of oncogene protein product in the cytoplasm of its cells and the frozen section from the tissue sample taken from the patient. Both samples on the second slide are stained with the thionine stain and the alkaline phosphatase staining system. The first sample is quantitated for both DNA and the oncogene protein product so that the system can create a pair of linear equations relating the optical densities of the pixels sensed by the two optical trains to the known amounts of DNA and oncogene protein product in the calibration sample on the second slide.

The frozen section cell sample containing what may be cancer cells is then examined using the apparatus. Since the cancer cells of the frozen section do not have well defined borders, it is impractical to allow the apparatus and or the human operator to assign areas of the image field uniquely associated with single cells. As a result, the optical densities of the pixels associated with the red chromogen as detected by the 500 nanometer optical train, and exceeding a second preselected threshold, are summed for the entire image field to provide a summed or total value for the amount of oncogene protein product in the cells in the image field. The total amount of DNA in the image field is also determined by summing the pixels of the image from the 620 nanometer optical train exceeding the first threshold to yield a total for the amount of DNA in the cells in the image field.

The amount of DNA in the image field is divided by the average value for the DNA in the whole cell sample previously determined by examination of the touch preparation thereby yielding the sum total of whole and fractional cells in the image field. The image field cell total for the image field is then stored. The total amount of oncogene protein product is then divided by the image field cell total to yield the amount of oncogene protein product per cell in the image field.

It is principal aspect of the present invention to provide a method and apparatus for quantitating an amount of oncogene protein product for a tissue sample.

It is another aspect of the present invention to provide a method and apparatus for determining an amount of an oncogene protein product in a frozen section of a tissue sample.

Other aspects and advantages of the present invention will become obvious as one peruses the specification and claims in light of the accompanying drawings.

BRIEF DESCRIPTION OF THE DRAWINGS

FIG. 1 is an isometric view of an apparatus for determining an amount of an oncogene protein product embodying the present invention;

FIG. 3 is an elevational view of an optical conversion module of the apparatus of FIG. 1;

FIG. 10 is a depiction of a display screen shown by the system displaying a histogram of the per cell cytoplasmic mass in optical density units, of a set of control cells;

FIG. 11 is a depiction of a display screen shown by the system displaying a histogram of the per cell DNA or nuclear mass of a set of control cells;

FIG. 13 is a depiction of a screen display shown by the system displaying the average number of picograms of oncogene protein product per cell from a frozen section from a patient.

DETAILED DESCRIPTION OF THE PREFERRED EMBODIMENT

Figure 2:
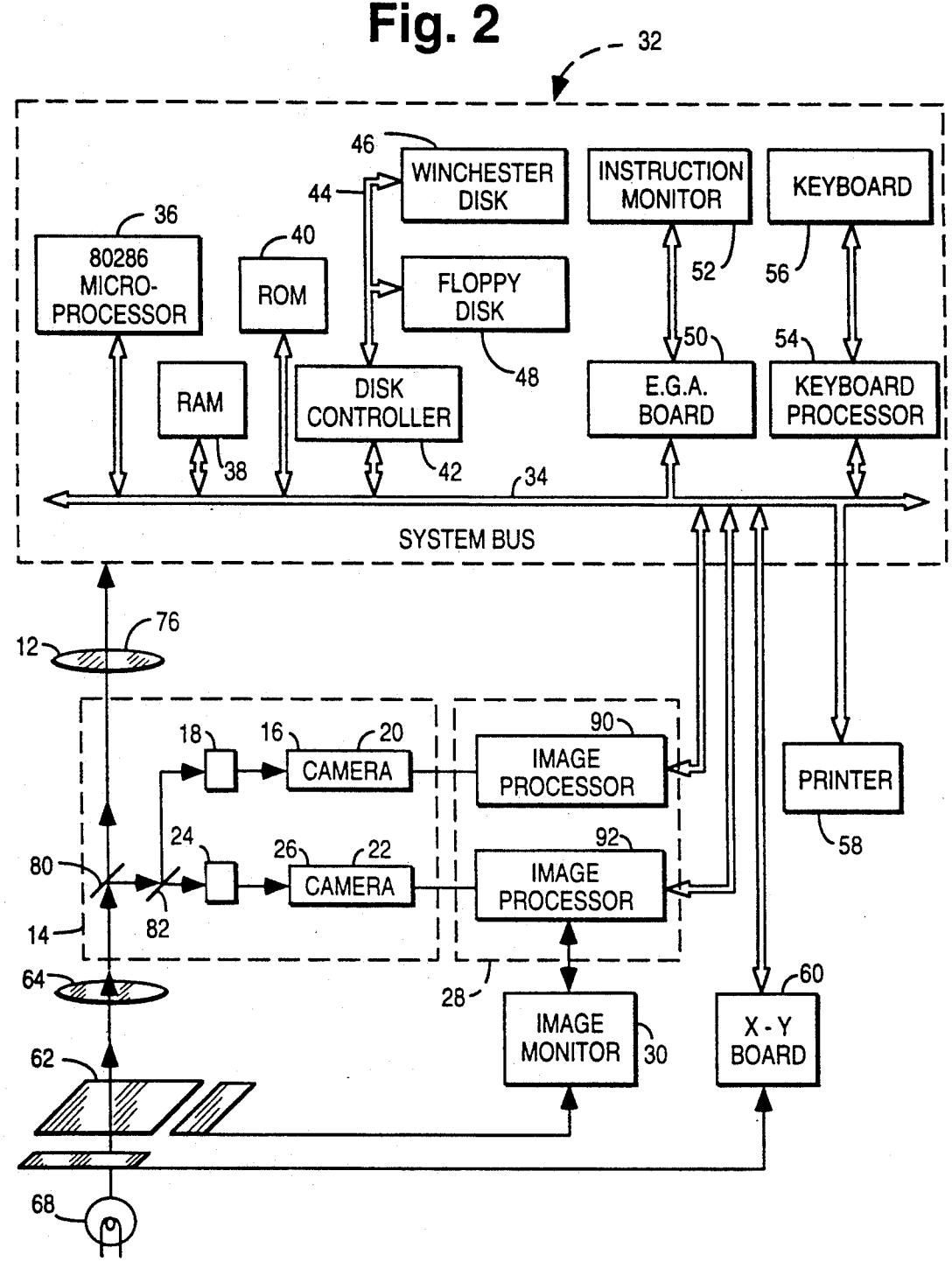
FIG. 2 is a block diagram of the apparatus of FIG. 1.

Referring now to the drawings and especially to FIG. 1, an apparatus embodying the present invention and generally identified by numeral 10 is shown therein. The apparatus 10 comprises an optical microscope 12, which may be of any conventional type but in this embodiment is a Reichart Diastar or Microstar. An optical conversion module 14 is mounted on the microscope 12 to enhance optically a magnified image of a cell sample viewed with the microscope 12. The optical conversion module 14, as may best be seen in FIG. 3, has a cell nuclei or DNA sensing means comprising a cell nuclei image optical enhancement unit 16. The cell nuclei image optical enhancement unit 16 has a 620±20 nanometer red narrow bandpass optical transmission filter 18 and a television camera 20 for receiving a filtered image from the filter 18. An oncogene protein product sensing means comprising an oncogene protein product optical enhancement module 22 has a green 500±20 nanometer narrow bandpass optical transmission filter 24 and a television camera 26 and is also part of the optical conversion module 14. Each of the television cameras 20 and 26 generates a standard NTSC compatible signal representative, respectively, of an enhanced DNA or cell nuclear material image and an enhanced oncogene protein product image. An image processing system 28 is connected to the television cameras 20 and 26 to receive the enhanced DNA image signal and the enhanced oncogene protein product image signal and to store a DNA pixel array and an oncogene protein product pixel array therein. The image processor 28 is connected to a computer 32, in the present embodiment, an IBM personal computer model AT for processing of the DNA and oncogene protein product pixel arrays.

The computer 32 includes system bus 34, connected to the image processor unit 28. An 80286 microprocessor 36 is connected to the system bus 34. A random access memory 38 and a read only memory 40 are also connected to the system bus 34 for storage of information. A disk controller 42 is connected by a local bus 44 to a Winchester disk drive 46 and to a floppy disk drive 48 for secondary information storage. A video conversion board 50, in this embodiment an, EGA board having 256K bytes of memory, is connected to the system bus 34 to control an instruction monitor 52 connected to the EGA board 50. A keyboard processor 54 is connected to the system bus 34 to interpret signals from a keyboard 56 which is connected to the keyboard processor 54. A printer 58 is connected to the system bus 54 for communication therewith. An X Y or image field board 60 is connected to the system bus 34. The X Y board 60 also is connected to a slide holder of the microscope 12 to sense the relative position of a slide 62 with respect to a microscope objective 64 and thus identify a field being viewed. Included are a Y position sensor 66 and an X position sensor 68. The Y position sensor 66 is connected via a communication path 70 to the X Y board 60. The X position sensor 68 is connected via a communication path 72 to the X Y board 60. The microscope 12 also includes an eyepiece 76 in optical alignment with the objective 64 for magnification of light forming an image of a cell sample on the slide 62.

The method of the instant invention is practiced by collecting a cell sample, which may be in the form of a tissue section made from a frozen section or a paraffinized section and having both cell nuclei, cell fragments and whole cells therein. The cells of the cell sample are placed on the slide 62 and fixed thereon. A rabbit monoclonal antibody for a protein product of the neu HER-2 proto-oncogene to be detected in the cells is then placed in contact with them. The monoclonal antibody selectively binds to all points on and within the cells where the neu HER-2 protein product is present. The monoclonal antibody also has bound thereto a bridging anti-rabbit mouse antibody and an alkaline phosphatase complex. The alkaline phosphates complex comprises an anti-mouse antibody which also specifically binds to the alkaline phosphatase enzyme. The alkaline phosphatase enzyme is bound to the antibody and held through the chain of antibodies to the neu HER-2 protein product in the cells.

In order to view and measure the oncogene protein product sites, a quantity of a mixture containing Napthol ASTR and Fast Red KL chromogen is applied to the cell sample on the slide. The Napthol ASTR and the Fast Red KL react to form a red azo chromogen. The usual rate of reaction however is relatively low. The alkaline phosphatase catalyzes the chromogen-forming reaction only at the points where the alkaline phosphatase is localized. Thus, red chromogen is found only at the points in the cells where protein product of the neu HER-2 oncogene is present and the cells are preferentially stained only at the points where they have the oncogene protein product. After a period, any remaining unreacted Napthol ASTR and Fast Red KL chromogen are removed from the cell sample. The cells are then stained with a thionine stain using the Feulgen technique which leaves a blue stain preferentially bound with the DNA in the cell nuclei. Thus, the DNA is stained blue and the points within the cells having oncogene protein product are stained red.

The microscope slide 62 is then placed on a carrying stage of the microscope 12 and the objective 64 is focused thereon. Light from the objective 64 travels through the eyepiece 12 where it may be viewed by an observer. In addition, the optical converter module 14 includes a beam-splitting mirror 80 which carries off approximately 90% of the light to other portions of the converter. The light is fed to a dual prism dichroic mirror 82 which reflects a portion of the light to the red filter 18. The remaining portion of the light is filtered by the dichroic mirror 82 and fed to the green filter 24. The dichroic mirror 82 selectively passes light having wavelengths greater than 500 nanometers to the filter 18 and having a wavelength of less than 500 nanometers to the filter 24. Thus, the dichroic mirror 82 acts as a first color filter before the light reaches the color filters 18 and 24.

Figure 7:
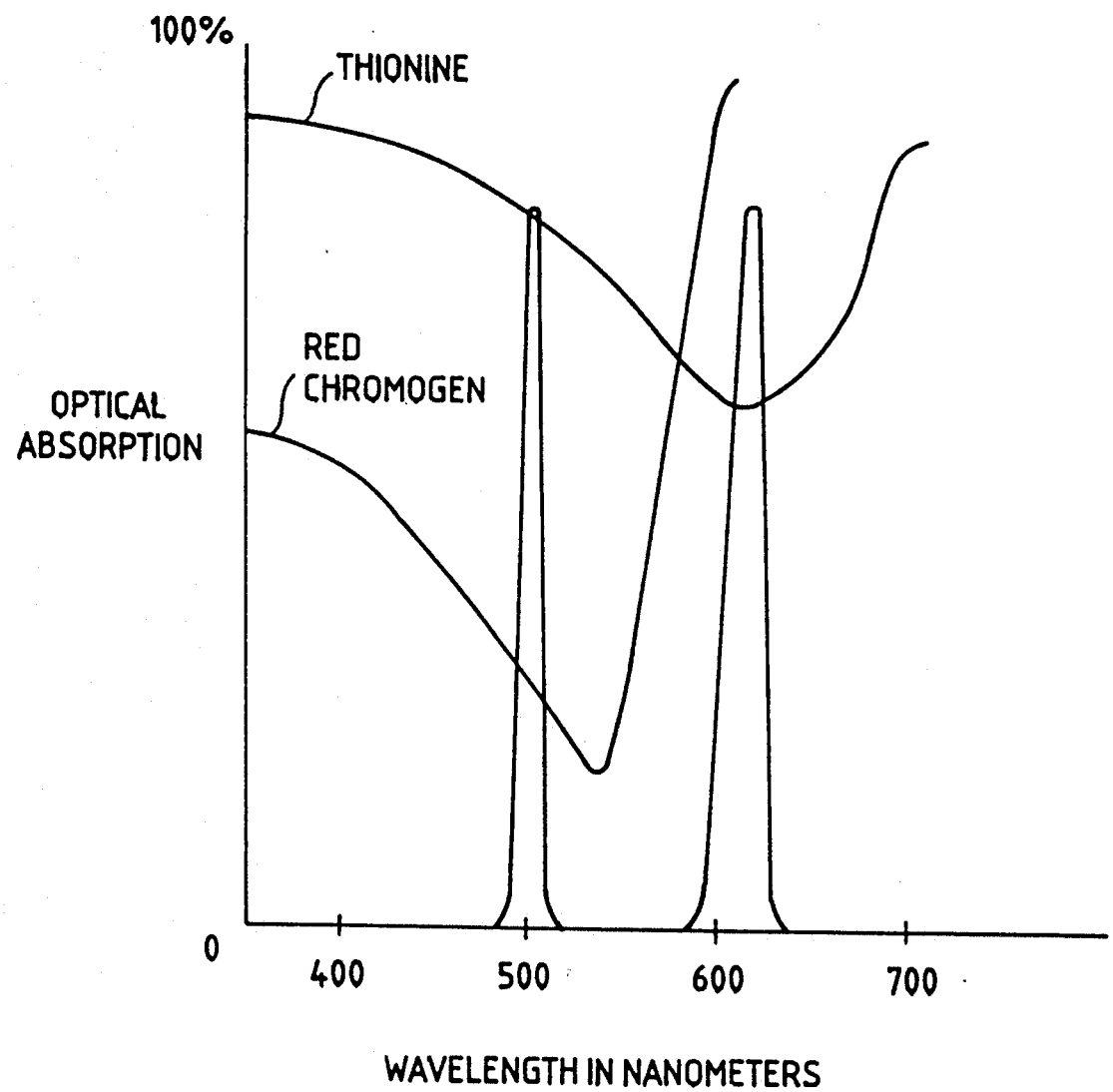
FIG. 7 is a graph of the spectral response of a red chromogen, a thionine stain and the narrow band optical filters.

When the light passes through the filter 18, the filter 18 preferentially blocks light from the blue stained DNA and provides a high contrast cell nuclei image to the camera 20. The optical characteristics of the blue stain and the red chromogen, as well as the optical filters 18 and 24 are shown in the graph of FIG. 7. The camera 20 then generates an NTSC DNA image signal which is fed to the image processor module 28. The image processor module 28 has an image processor 90 and an image processor 92. Each of the image processors 90 and 92 is a model AT428 from the Datacube Corporation. Similarly, the green filter 24 provides a high contrast oncogene protein product image to the camera 26. The camera 26 then feeds the oncogene protein product image signal to the image processor 92. Both of the image processors 90 and 92 contain analog to digital converters for converting the analog NTSC signals to digitized arrays of pixels which are then stored within internal frame buffers. The internal frame buffers may be accessed via the system bus 34 under the control of the microprocessor 36.

Figure 4:
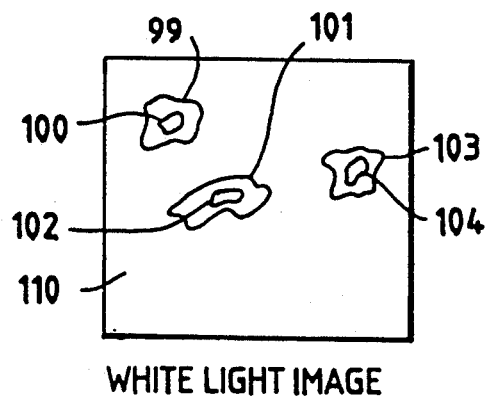
FIG. 4 is a magnified view of a stained cell sample as seen through the microscope of FIG. 1 without optical filtering.

The image of the cell sample viewed through the eyepiece 12 is of the type shown in FIG. 4 having red cytoplasm 99 and a blue cell nucleus 100, red cytoplasm 101 and a blue cell nucleus 102, and red cytoplasm 103 and a blue cell nucleus 104. As may best be seen in FIG. 5, the cells are shown therein as they would appear through the red filter 18, which causes all of the blue stained DNA to darken and appear prominently. As may best be seen in FIG. 6, the oncogene protein product image of the cell nuclei of FIG. 4 is shown therein with the DNA of the cell nuclei 100, 102 and 104 being rendered substantially transparent or invisible by the effect of the 500 nanometer filter 24. The 500 nanometer filter 24 transmits at an optical absorbing region of the red stain and at an optical transmission region of the blue stain. The 620 nanometer filter transmits at an optical absorbing region of the blue stain and at an optical transmission region of the red stain. The cytoplasm 99, 101 and 103 having the red chromogen deposited therein, which is an indicator for the protein product of the oncogene, appears clearly in high contrast.

Figure 5:
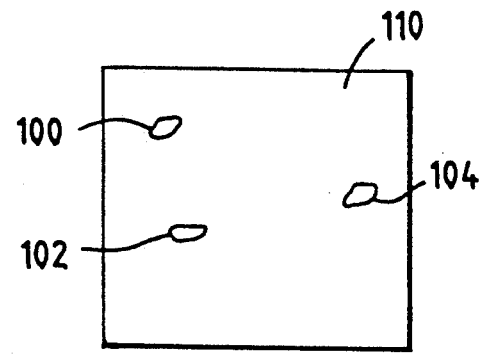
FIG. 5 is a magnified view of the stained cell sample of FIG. 4 as seen through a 620 nanometer narrow band optical filter which yields a DNA or nuclear material image.
Figure 6:
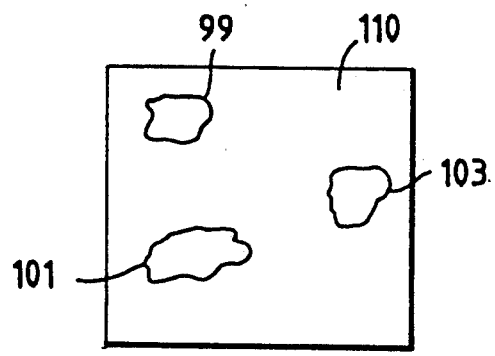
FIG. 6 is a magnified view of the stained cell sample of FIG. 4 as seen through a 500 nanometer narrow band optical filter which yields an oncogene protein product image.

The image of FIG. 5 is stored in the internal frame buffer of the image processor 90. The image of FIG. 6 is formed and stored in the internal frame buffer of the image processor 92. It may be appreciated that the pixel values for the images may be sliced using standard image processing techniques to increase the contrast between the stained areas and the backgrounds. That is, the areas of high optical density in FIG. 6 the cytoplasm 99, 101 and 103 are shown as being very dense and stored as high optical density pixels, while the background areas 110 may be stored as substantially zero optical density pixels in order to provide a clear threshold or difference between the two areas.

Figure 8:
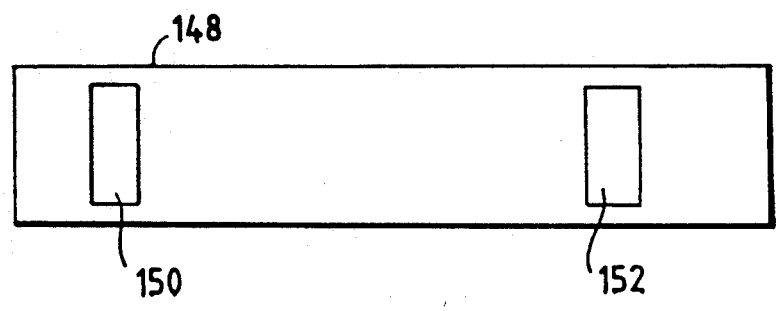
FIG. 8 is an elevational view of a microscope slide including a calibration zone.
Figure 9:
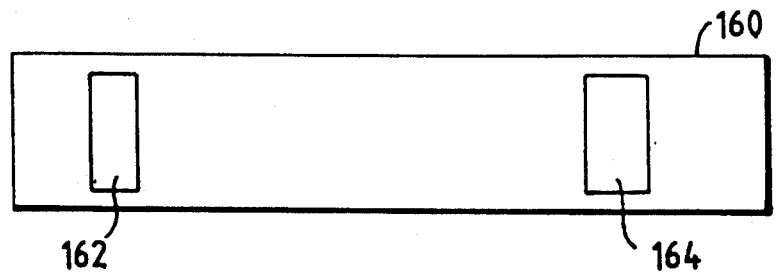
FIG. 9 is an elevational view of a second microscope slide including a calibration zone.

Although the general of processing the images of the stained is disclosed above a more detailed of the invention follows. As may best be seen in FIG. 8, a first slide 148 includes a DNA or nuclear material calibration zone 150 and a whole cell preparation measurement zone 152. In the calibration zone 150 is a cell population having a known quantity of DNA, usually 7.18 picograms per cell nucleus in each of the cells. A whole cell preparation is positioned in the whole cell measurement zone 152 and is prepared by making a touch preparation from a frozen section taken from a human breast cancer tumor. The touch preparation is made simply by touching a warm slide to the frozen tumor tissue and allowing the cells from the frozen tumor tissue to cling to the warm slide. It may be appreciated that all of the DNA or nuclear material, including the entire cell nucleus, from the transferred cells clings to the whole cell preparation zone 152 and is thus pulled intact from the frozen tissue sample, although the associated cytoplasm may be damaged in the transfer. The standard cells in the calibration zone 150 and the cells of the whole cell preparation zone 152 are then stained with a the thionine stain using the Feulgen technique in order to optically enhance the DNA. The system then reads the slide 148 by having it placed on the microscope stage where the image is fed through both of the optical trains 16 and 22. The image received by the camera 20 consists of a darkened area where the DNA has been stained blue by the thionine stain and a substantially clear area outside it. The image is digitized and the resulting pixels are stored. The stored pixels are segregated into separate cell images. The pixel values exceeding the threshold are summed to give summed values of optical density for each of the cells in the calibration zone 150. A similar summing technique is employed for the cells of the whole preparation zone 152. The values are stored and may be displayed in histograms by the system, as shown in FIG. 11. The values also are averaged respectively, for the calibration cells and the whole cell preparation cells. Those averages are used to compute the average value of DNA mass per cell for the cells taken from the biopsied tissue and stained in the whole cell preparation zone 152. The average value of DNA mass per cell is used for later normalization of cytoplasm measurements from frozen sections. Since it is known that the summed optical density from the field from the calibration side is equivalent to a concentration of 7.18 picograms a linear equation can be developed relating the optical density of the image to the amount of DNA present in the imaged cells. Thus, the optical density of the summed pixels is measured on the right hand side of the slide 150 summed and sum value is inserted into the equation to compute the average quantity of DNA per cell in the frozen tissue section. If the cells are diploid cells, typically the average quantity will be 7.18 picograms. If the cells are tetraploid, which is often common with cancers, the cells will each typically have 14.36 picograms of DNA per cell nucleus.

Figure 12:
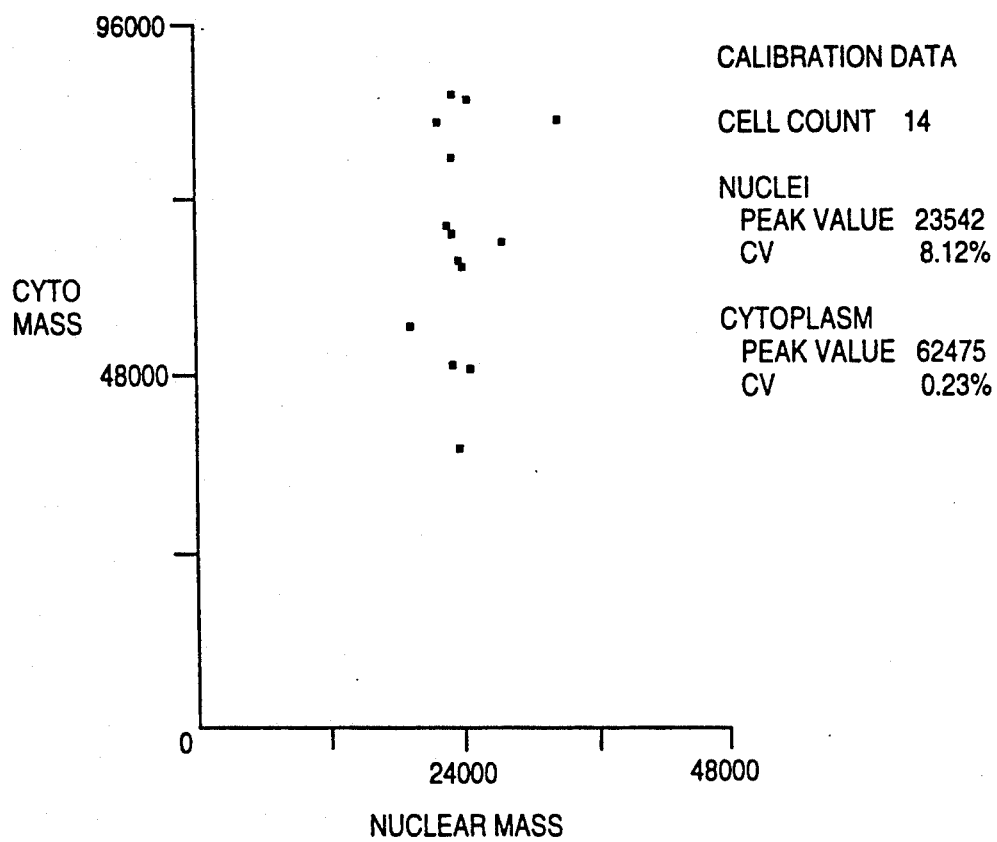
FIG. 12 is a depiction of a display screen shown by the system displaying a scattergram of the cytoplasmic mass versus the DNA or nuclear mass of the same cells.

Once the average amount of DNA per cell nucleus for a number of fields in the calibration slide have thus been determined, a second calibration slide 160 for calibrating the amount of oncogene protein product is then prepared. The second calibration slide 160 includes a calibration portion 162 having a plurality of cells taken from a standard cell line having a known amount of DNA per cell and a known amount of oncogene protein product per cell. An examination zone 164 on the slide 160 has frozen section of the tissue taken from a human patient who is to be evaluated. The standard cells in zone 162 and the sectioned cells in zone 164 are then contacted with an oncogene protein product rabbit antibody which attaches to the protein products of the neu HER-2 oncogenes present in the cells. A bridging mouse anti-rabbit antibody is conjugated with the rabbit antibody. An alkaline phosphatase antibody and alkaline phosphatase are conjugated to the mouse anti-rabbit antibody. Napthol ASTR and Fast Red KL are then placed on the slide and a red azo chromogen is formed at each of the locations where alkaline phosphatase is present. Thus, the cells in both zones are stained red in the areas in which oncogene protein product is present. The cells also are stained with the thionine stain using the Feulgen technique. This allows the areas having DNA to be identified and measured. The amounts of DNA and oncogene protein product are determined in the same manner as the DNA was quantitated. The system thus has stored therein the average amount of DNA and oncogene protein product per cell for the cells in the calibration zone 162. This allows staining variations to be calibrated out. The distributions of the per cell DNA and oncogene protein product amounts may be output to the user in the form of display information as may best be seen in FIGS. 10, 11 and 12.

Finally, the stained frozen tissue section is examined under the optical microscope. The cell images are fed through the 500 nanometer and 620 nanometer optical trains where respectively, summed optical densities, for the entire image field, of the DNA identified by the thionine stain and the neu HER-2 protein product identified by the red stain are computed. The total number of cells present in the image field under examination is computed by dividing the summed DNA mass by the average amount of DNA per cell, as derived from the measurements made on the whole cell preparation. The summed amount of oncogene protein product is then divided by the number of cells under examination to yield the amount of oncogene protein product per cell, which is output on the display, as may best be seen in FIG. 13. It is this value which will allow the clinician to formulate an appropriate course of action for the patient. Although the invention disclosed herein employs particular materials, it may be appreciated that various other materials may be used in its practice.

While there has been illustrated and described a particular embodiment of the present invention, it will be appreciated that numerous changes and modifications will occur to those skilled in the art, and it is intended in the appended claims to cover all of those changes and modifications which fall within the true spirit and scope of the present invention.

What is claimed is:

1. A method for determining an amount of an oncogene protein product per cell in a cell sample from which a tissue section and whole cell preparation are prepared, comprising the steps of:
    measuring an amount of DNA in a DNA calibration sample of cells having a known amount of DNA in each of the cells of the DNA calibration sample;
    producing a measured DNA calibration signal in response to said measured amount of DNA;
    producing a DNA calibration signal relating the amount of DNA to the measured DNA calibration signal;
    measuring an amount of an oncogene protein product in an oncogene protein product calibration sample of cells having a known amount of said oncogene protein product in the cells of the oncogene protein product calibration sample;
    producing a measured oncogene protein product signal in response to said measured amount of said oncogene protein product;
    determining the optical density of portions of said whole cell preparation and said tissue section prepared from said cell sample stained with a first stain specific for DNA;
    producing a DNA cell sample signal in response to the determination of the optical density of said first stain for said whole cell preparation and said tissue section prepared from said cell sample;
    producing a cell count signal for said whole cell preparation in response to said DNA cell sample signal for said whole cell preparation;
    determining the optical density of portions of said tissue section prepared from said cell sample stained with a second stain specifically related to said oncogene protein product;
    producing an oncogene protein product cell sample signal in response to the determination of the optical density of said second stain;
    producing a DNA cell sample amount signal in response to said DNA calibration signal and to said DNA cell sample signal for said whole cell preparation and said tissue section prepared from said cell sample;
    producing an average DNA per cell signal in response to said DNA cell sample amount signal for said whole cell preparation and said cell count signal for said whole cell preparation;
    producing a total cell number for said tissue section in response to said average DNA per cell signal and said DNA cell sample amount signal for said tissue section;
    producing an oncogene protein product copy amount signal in response to said total cell number for said tissue section and in response to said oncogene protein product cell sample signal; and
    producing an output signal in response to said oncogene protein product copy amount signal indicative of the amount of said oncogene protein product per cell in said cell sample.

2. A method of determining an amount of an oncogene protein product per cell in a cell sample, comprising the steps of:

optically enhancing the DNA in a whole cell preparation and tissue section taken from a tissue sample with a first image enhancing material;

optically enhancing the oncogene protein product in the cytoplasm of the tissue section with a second image enhancing material;

determining the average amount of DNA per cell in said whole cell preparation taken from the same tissue sample;

determining the total amount of oncogene protein product in the tissue section;

determining the total amount of DNA in the tissue section;

comparing the total amount of DNA to the average amount of DNA per cell to obtain the total number of cells in the tissue section being examined; and comparing the amount of oncogene protein product to the number of cells to obtain the amount of oncogene protein product per cell in the tissue section.

3. A method in accordance with claim 2 further comprising the steps of:

calibrating for at least one of the average amount and total amount of DNA by measuring the DNA in a DNA calibration cell sample; and calibrating for the amount of oncogene protein product by measuring the amount of said oncogene protein product in a oncogene protein product calibration cell sample.

4. An apparatus for determining an amount of an oncogene protein product per cell in a cell sample from which a tissue section and whole cell preparation are prepared, comprising:

means for measuring an amount of DNA in a DNA calibration sample of cells having a known amount of DNA in each of the cells;

means for producing a measured DNA calibration signal in response to said measured amount of DNA;

means for producing a DNA calibration signal relating the amount of DNA to the measured DNA calibration signal;

means for measuring an amount of an oncogene protein product in an oncogene protein product calibration sample of cells having a known amount of said oncogene protein product per cell in the cells of the oncogene protein product calibration sample;

means for producing a measured oncogene protein product signal in response to said measured amount of said oncogene protein product;

means for determining the optical density of portions of said whole cell preparation and said tissue section prepared from said cell sample stained with a first stain specific for DNA;

means for producing a DNA cell sample signal in response to the determination of the optical density of said first stain for said whole cell preparation and said tissue section prepared from said cell sample;

means for producing a cell count signal for said whole cell preparation in response to said DNA cell sample signal for said whole cell preparation;

means for determining the optical density of portions of said tissue section prepared from said cell sample stained with a second stain specifically related to said oncogene protein product;

means for producing an oncogene protein product cell sample signal in response to the determination of the optical density of said second stain;

means for producing a DNA cell sample amount signal in response to said DNA calibration signal and to said DNA cell sample signal for said whole cell preparation and said tissue section prepared from said cell sample;

means for producing an average DNA per cell signal in response to said DNA cell sample amount signal for said whole cell preparation and said cell count signal for said whole cell preparation;

means for producing a total cell number for said tissue section in response to said average DNA per cell signal and said DNA cell sample amount signal for said tissue section;

means for producing an oncogene protein product copy amount signal in response to said total cell number for said tissue section and in response to said oncogene protein product cell sample signal; and means for producing an output signal in response to said oncogene protein product copy amount signal indicative of the amount of said oncogene protein product per cell in said cell sample.

5. An apparatus for determining an amount of an oncogene protein product per cell in a cell sample having DNA therein, which DNA is optically enhanced with a first image enhancing material in a whole cell preparation and a tissue section taken from a tissue sample, and having oncogene protein product which is optically enhanced with a second image enhancing material in the cytoplasm of said tissue section, comprising:

means for determining the average amount of DNA per cell in said whole cell preparation taken from the same tissue sample;

means for determining the total amount of oncogene protein product in the tissue section;

means for determining the total amount of DNA in the tissue section;

means for comparing the total amount of DNA to the average amount of DNA per cell to obtain the total number of cells in the tissue section being examined; and means for comparing the total amount of oncogene protein product to the number of cells to obtain the amount of oncogene protein product per cell in the tissue section.

6. An apparatus in accordance with claim 5 further comprising:

means for calibrating for the amount of both the average amount of DNA per cell in said whole cell sample and the total amount of DNA in the tissue section by measuring the DNA in a DNA calibration cell sample; and means for calibrating for the oncogene protein product by measuring the amount of said oncogene protein product in an oncogene protein product calibration cell sample.

* * * * *

UNITED STATES PATENT AND TRADEMARK OFFICE
CERTIFICATE OF CORRECTION

PATENT NO. : 5,252,487
DATED : October 12, 1993
INVENTOR(S) : Bacus, et. al.

It is certified that error appears in the above-indentified patent and that said Letters Patent is hereby corrected as shown below:

Title page, [57] Abstract, line 6, delete "protein product" (second occurrence).
line 9, delete " protein product" (second occurrence)

Column 3, line 18, after "chromogen, " delete "v".
Column 4, line 66, after "principal" isnert --a--.
Column 5, line 36, after "mass" insert --;--.
Column 8, lines 20-22, change "of processing the images of the stained" to --processing of the stained images--.
Column 8, line 41, delete "the".
Column 9, line 64, delete "." (first occurrence).
Column 11, line 29, change "a" to --an--.

Signed and Sealed this

Seventeenth Day of May, 1994

Attest:

BRUCE LEHMAN

*Attesting Officer*   *Commissioner of Patents and Trademarks*